United States Patent [19]

Papierski et al.

[11] Patent Number: 5,437,667
[45] Date of Patent: Aug. 1, 1995

[54] DYNAMIC EXTERNAL FIXATOR FOR THE WRIST

[75] Inventors: Paul E. Papierski, Redlands, Calif.; Frank J. Hauptmann, Mundelein, Ill.

[73] Assignee: Innovative Orthopaedics, Manufacturing, Inc., Mundelein, Ill.

[21] Appl. No.: 255,112

[22] Filed: Jun. 7, 1994

Related U.S. Application Data

[63] Continuation of Ser. No. 972,998, Nov. 11, 1992, abandoned.

[51] Int. Cl.$^6$ ................................................ A61F 5/04
[52] U.S. Cl. ........................................ 606/55; 606/59
[58] Field of Search ....................... 606/53, 54, 55, 56, 606/57, 58, 59, 72, 73; 602/21

[56] References Cited

U.S. PATENT DOCUMENTS

| 3,941,123 | 3/1976 | Volkov et al. | 606/55 |
| 4,628,919 | 12/1986 | Clyburn | 606/55 |
| 4,696,293 | 9/1987 | Ciullo | 606/55 |
| 4,730,608 | 3/1988 | Schein | 606/54 |
| 4,782,842 | 11/1988 | Fietti, Jr. | 606/54 |
| 4,919,119 | 4/1990 | Jonsson et al. | 606/54 |
| 4,922,896 | 5/1990 | Agee et al. | 606/55 |
| 4,988,349 | 1/1991 | Pennig | 606/58 |
| 5,122,140 | 6/1992 | Asche et al. | 606/55 |

Primary Examiner—Peter A. Aschenbrenner
Assistant Examiner—Guy V. Tucker
Attorney, Agent, or Firm—Gardner, Carton & Douglas

[57] ABSTRACT

A device for dynamic external fixation of a distal fracture of the radius having a proximal leg fixed to the radius and a distal leg fixed to the metacarpal using fixation pins. The proximal and distal legs of the external fixator are connected by a hinge mechanism, which defines a range of flexion and extension of the wrist, and a track-track housing mechanism, which defines a range of radial and ulnar deviation of the wrist. The axis of movement of the hinge mechanism and the axis of movement of the track-track housing mechanism passes through the proximal pole of the capitate bone.

35 Claims, 5 Drawing Sheets

DYNAMIC EXTERNAL FIXATOR FOR THE WRIST

This is a continuation of application Ser. No. 07/972,998 filed Nov. 11, 1992, now abandoned.

FIELD OF THE INVENTION

The present invention relates generally to devices for use in osteosynthesis of a fracture, and more particularly to an external dynamic fixator used for osteosynthesis of a fracture of the distal radius.

BACKGROUND OF THE INVENTION

External fixation and skeletal immobilization was first described by Boehler, who popularized this technique using pins and plaster in 1929. In 1944, Roger Anderson and Gordon O'Neil introduced the concept of external fixation using an external frame to hold skeletal fixation pins rather than plaster. These fixators are used for comminuted unstable distal radius fractures, both with and without internal fixation of the fracture fragments themselves. External fixation is generally indicated for fractures that have comminution and that are unstable. The rationale for this approach is that the unstable fracture tends to displace despite external support, if the dorsal bone fragments cannot be locked into some semblance of stability. With the palmar fracture line acting as a fulcrum, the compressive force acting along the radial articular surface favors redisplacement. If the applied tensile forces provided by an external fixator can be incorporated across the wrist, this tendency to angular compressive displacement will be minimized.

External fixation can be accomplished with the pins and plaster technique more recently described by Green in his paper, "Comminuted Fractures of the Distal End of the Radius." Green reported excellent results in seventy-five comminuted distal radius fractures treated by this method. Other methods include several available external fixators.

The use of external fixators for the treatment of unstable and comminuted intra-articular distal radius fractures is well established as noted by W. P. Cooney in his paper "External Pin Fixation for Unstable Colles Fractures" as well as Grana and Kopta in their paper, "The Roger Anderson Device and the Treatment of Fractures of the Distal End of the Radius."

Current designs include both static models which hold the fracture in a stable position and dynamic external fixators which allow for some movement. The advantages of external fixators over the pins and plaster technique are facilitation of pin care, absence of constricting casts, lighter weight and ease of wound care; and for dynamic external fixators, wrist motion is allowed while maintaining traction at the fracture site. This last feature is important as wrist motion has been shown to improve the functional results in intra-articular fractures. This was suggested in the papers by Nakata et al., "External Fixators With Wrist Fractures: A Biomechanical and Clinical Study" as well as Salter et al., "The Biological Effects of Continuous Passive Motion on the Healing of Defects in Articular Cartilage."

Generally, fixators employ the principal of longitudinal traction applied to the skeleton by proximal and distal pins at either end of the bone which is fractured. In the case of the wrist, this occurs across the wrist joint, with proximal pins in the radial shaft and distal pins in the metacarpal bones. The benefits to be gained by dynamic external fixators is to allow the combination of stability of the distal radius fracture while allowing freedom of movement of the joint itself. This procedure allows earlier recovery from the stiffness normally associated with immobilization of the fracture while maintaining adequate alignment of the bony fracture itself during the process of healing.

Ideally, the external fixator used in the treatment of comminuted intra-articular fractures of the distal radius should have sufficient rigidity to maintain length and reduction of fracture fragments while allowing motion at the wrist joint. Allowing motion of the wrist and digits after the treatment of distal radius fractures, often with the calculated risk of some loss of reduction, has been advocated especially by Lidstrom in his paper entitled, "Fractures of the Distal End of the Radius: A Clinical and Statistical Study of End Results."

Although a number of prior art dynamic external fixators have been proposed, the dynamic external fixator of the present invention represents a substantial and fundamental advance over prior art devices in that it recognizes that the range of motion defined by the device should precisely correspond to the normal kinematic motion of the wrist. Normal kinematic motion of the wrist is described for example, by Youm and Flatt in their paper, "Kinematics of the Wrist I: An Experimental Study of Radial Ulnar Deviation and Flexion-Extension." According to a preferred embodiment, the present invention does not allow movement which deviates from the normal kinematic movement of the wrist. Furthermore, in order to promote healing, the device of the present invention may be adjusted to limit the range of motion to a portion of the full range of motion of the human wrist. These and other advantages of the present invention will become apparent from a reading of the following detailed description of the preferred embodiment.

SUMMARY OF THE INVENTION

It is an object of the present invention to provide a dynamic external fixator for use in osteosynthesis of a fracture of the distal radius which precisely defines a range of movement that substantially corresponds to the normal kinematic movement of the human wrist.

It is another object of the present invention to provide such a dynamic external fixator that does not allow movement that deviates from the normal kinematic movement of the wrist.

It is another object of the present invention to provide such a dynamic external fixator that is adjustable so that the range of movement may be limited to a portion of the full range of normal kinematic movement of the wrist.

It is a related object of the present invention to provide such a dynamic external fixator that may be selectively adjusted to define any range up to a maximum degree of flexion, a maximum degree of extension, a maximum degree of ulnar deviation and a maximum degree of radial deviation.

It is also an object of the present invention to provide such a dynamic external fixator that may be precisely affixed to the lower arm and hand of a patient so that the range of motion defined by the fixator is aligned with the range of normal kinematic motion of the patient.

These and other objects are realized in the present invention which provides a dynamic external fixation device for osteosynthesis of a fracture of the distal radius which defines a range of movement that substantially corresponds to the normal kinematic movement of the human wrist. According to a preferred embodiment, the device includes proximal and distal legs which are connected to a hinge mechanism, which defines a range of flexion and extension of the wrist, and a track-track housing mechanism, which defines a range of radial and ulnar deviation of the wrist. The axis of movement defined by the hinge mechanism and the axis of movement defined by the track-track housing mechanism passes through the proximal pole of the capitate bone.

These and other objects and aspects of the present invention may be better understood through the following detailed description of the preferred embodiment of the invention when taken in conjunction with the accompanying drawings.

While the invention will be described in connection with certain preferred embodiments, it will be understood that such description is not intended to limit the invention to those embodiments. On the contrary, it is intended to cover all alternatives, modifications and equivalents as may be included within the spirit and scope of the invention as defined by the appended claims.

DETAILED DESCRIPTION OF THE PREFERRED EMBODIMENT

Figures 3, 4:
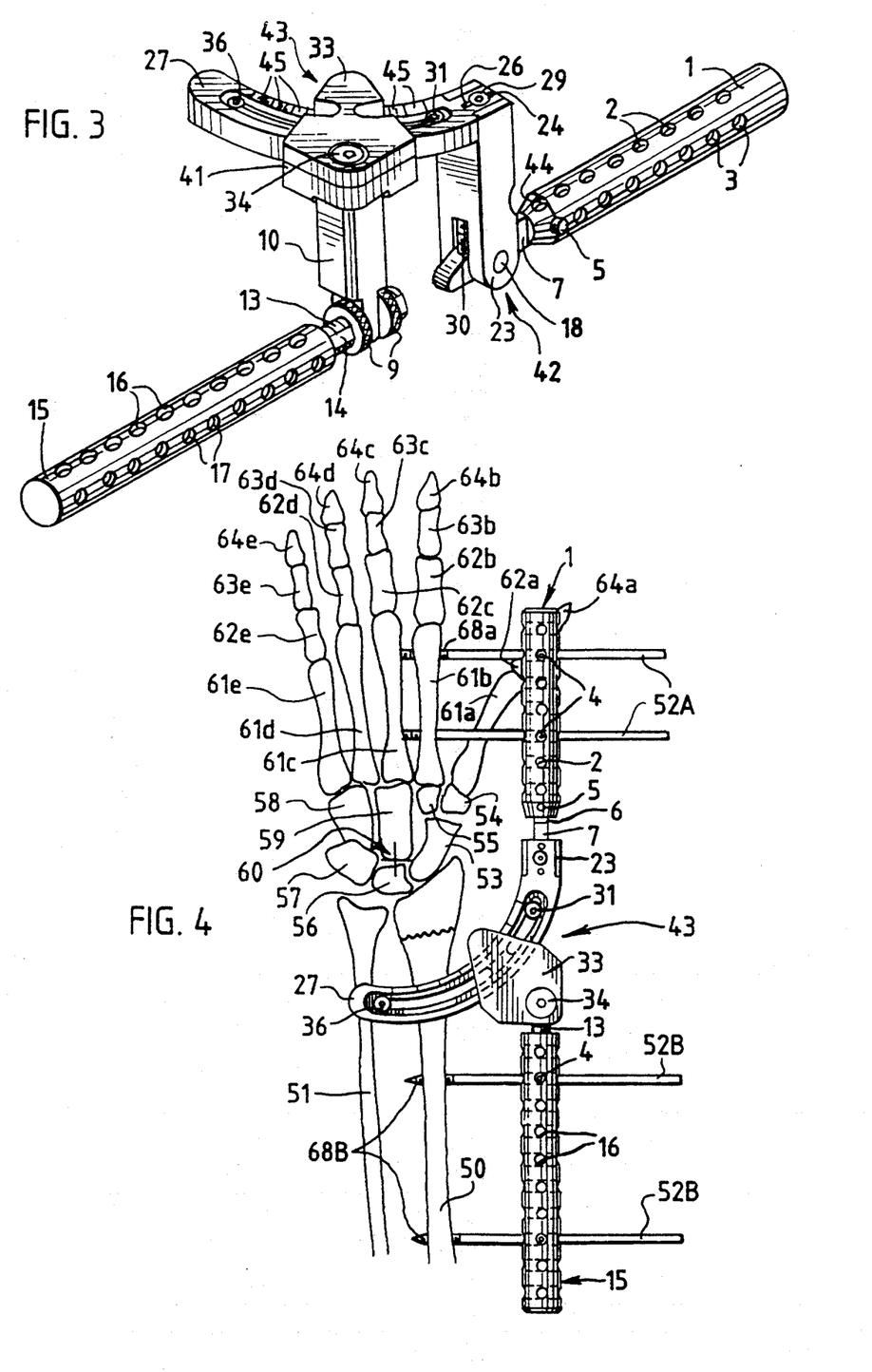
FIG. 3 shows an isometric view of the dynamic external fixator of the present invention.
FIG. 4 shows a top view of distal portions of the radius and ulnar of an arm in conjunction with the bones of the wrist and hand thereof with the apparatus of the present invention fastened thereto.

Turning initially to FIG. 3, there is shown a dynamic external fixation device in accordance with a preferred embodiment of the present invention. The device is comprised of a distal leg 1 and a proximal leg 15 connected in series to a hinge mechanism 42 and track-track housing mechanism 43. Preferably, the proximal 15 and distal 1 legs are cylindrical in shape. As shown in FIG. 4, in order to securely retain bone fixation pins 52, the proximal 15 and distal 1 include a first set of holes 17 drilled completely through and having smooth bores, while a second set of holes 16, which are drilled and tapped, are arranged perpendicular to the smooth holes 17. Before the device is attached to the hand, but after the distal bone fixation pins 52 are affixed to the metacarpal bones 61b and 61c, the distal leg 1 may be rotated axially on the distal leg stem 7 by means of the threaded portion 6 onto which the distal leg 1 is attached, in order to facilitate receiving the pins 52A within the smooth holes 17. The position of the distal leg 1 on the distal leg stem may be securely maintained by means of a threaded screw 5 inserted into hole 44 at the proximal end of the distal leg 1. The threaded screw 5 holds the distal leg 1 onto the threaded portion 6 of the distal leg stem 7 by direct pressure of the screw 5 bearing against the stem 7.

The dynamic external fixator of the present invention, when properly affixed to the lower arm and hand, maintains tension across the fracture and wrist joint separating the adjacent bones and tightening the ligaments connecting these bones. This tension maintains alignment of the fractured bone in a manner similar to placing tension on a string of beads, thus aligning the beads. The device is preferably made of a material capable of withstanding sterilizations, such as aluminum, since all components of the device should be capable of being gas sterilized or steam autoclaved.

According to an important aspect of the present invention, relative movement between the distal leg 1 and proximal leg 15 is controlled by an articulating mechanism which defines a range of movement for the attached wrist that corresponds substantially to the normal kinematic movement of the human wrist. According to a preferred embodiment of the invention, the articulating mechanism is comprised of an track-track housing mechanism 43 that defines a range of radial and ulnar deviation and a hinge mechanism 18 that defines a range of flexion and extension. The movement of the track-track housing mechanism 43 and the hinge mechanism 42 is precisely guided so as to preclude movement of the wrist that deviates from the normal kinematic movement of the wrist.

Figure 5:
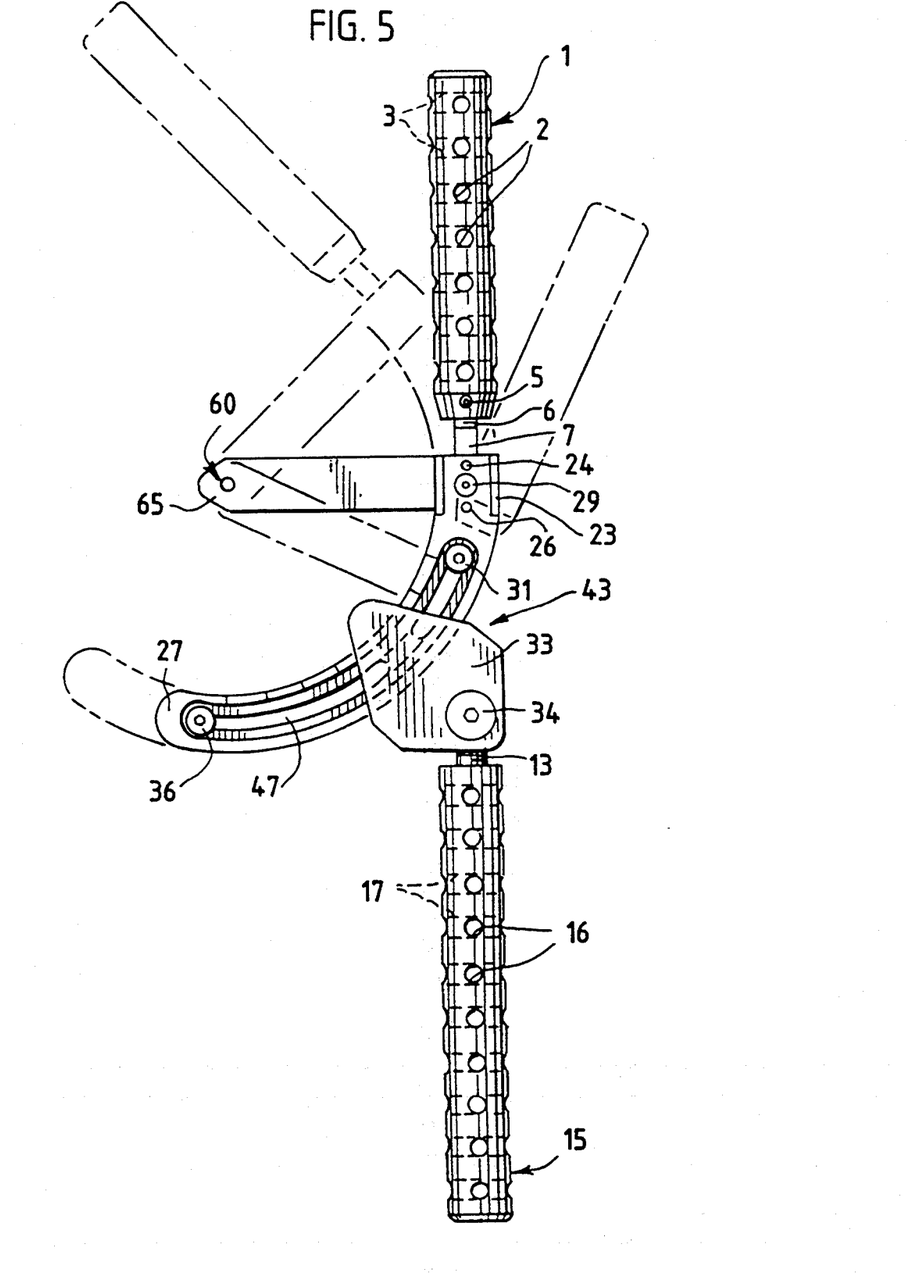
FIG. 5 shows a top view of the dynamic external fixator in radial and ulnar deviation.

The track-track housing mechanism 43 is comprised of a track housing 41 and a curved track 27 which is precisely guided as it slides through the track housing 41, as illustrated in FIG. 5. According to an important aspect of the present invention, the track-track housing mechanism 43 has an axis 60 corresponding to the axis of radial and ulnar deviation of the normal human wrist 60. The articulating mechanism also includes a hinge mechanism 42 connected between the track-track housing mechanism 43 and the distal leg stem 7 via an interconnect piece 23. The axis of the hinge 18 is aligned with and corresponds to the axis of flexion and extension of the normal wrist. Therefore, when the device is affixed, the normal axis of movement of the wrist, i.e. without a fracture, is essentially the same as the axis of the external fixator of the present invention.

Figure 8:
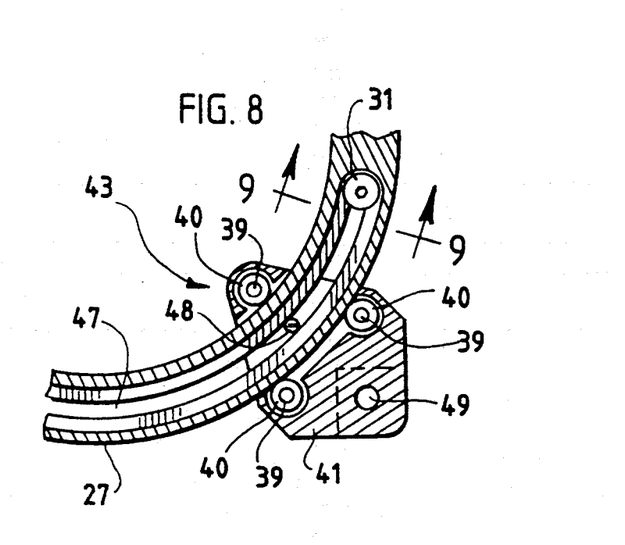
FIG. 8 is a section view taken at 8—8 of FIG. 2 depicting details of the track-track housing mechanism.
Figure 9:
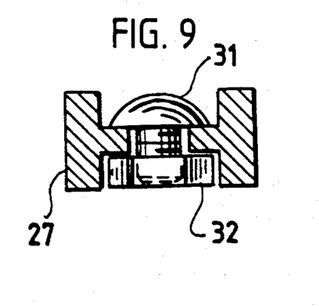
FIG. 9 is a section view taken at 9—9 of FIG. 8 depicting stops located within the track.

The track 27 is slotted 47 along its center, in order to receive a center pin 48 (FIG. 8) extending from and connected to the track housing 41. As shown in FIG. 9, the cross section of the portion of the track 27 with the slot 47, appears as two opposing shoulders that guide the pin 48 within. Two adjustable stops 31, 36, consisting, perhaps, of a screw 31 and a nut 32 (FIG. 9) are attached within the slot 47 of the track 27 so as to limit the number of degrees of movement allowed of the track 27 within the track housing 41. The two stops 31, 36, which are placed within the slot 47 on either side of the center pin 48, act to limit the full range movement of the track 27 within the track housing 41. Preferably, the track 27 will be provided with a set of graduation marks 45 to provide a reference as to the location of stops 31, 36 within the slot 47. A plurality of bushings 40 carried upon bushing pins 39 bear upon the inner and outer sides of the track 27, in order to guide the track 27 within the track housing 41. In addition to reducing friction during movement of the track 27 relative to the track housing 41, bushings 40 together with center pin 48 operate to reduce rocking or twisting of the track 27 within the housing 41 and, when operated in association with the other elements of the device, precisely define a range of movement of the track 27 relative to the housing 41 that corresponds substantially to the radial and ulnar deviation of the normal human wrist.

The cap 33 and bottom portions of the track housing 41 precisely control movement of the track 27 within the housing 41 and along the direction of radius of curvature of the track 27. The movement of the track 27 and attached distal leg 1 with respect to the track housing 41 and the proximal leg 15 is clearly illustrated in FIG. 5.

As shown in FIG. 4, the track 27 and track housing 41 are, when the device is affixed to the hand, generally located dorsally, i.e., to the back of the hand. The track housing 41 is connected to the proximal leg 15 of the dynamic external fixator by means of a proximal interconnection piece 10 which is mounted at the distal threaded end 13 of the proximal leg 15 of the dynamic external fixator and is directed in the dorsal or backward direction from the hand. The position of the proximal interconnecting piece 10 along the axis of the proximal leg 15. Adjustment of the knurled nuts 9, therefore, result in adjustment of the proximal leg 15 with respect to said distal leg 1. Rotation of the proximal interconnecting piece 10 upon the proximal leg 15 is prevented by a flat 14 on the threaded end 13 of the proximal leg 15, as illustrated in FIG. 2.

Attached to track 27 is a distal interconnecting piece 23 that extends between the track 27 and the hinge mechanism 18. The distal interconnecting piece 23 serves to position and secure the track 27 in alignment with the track housing 41, as illustrated in FIG. 2.

Figure 1:
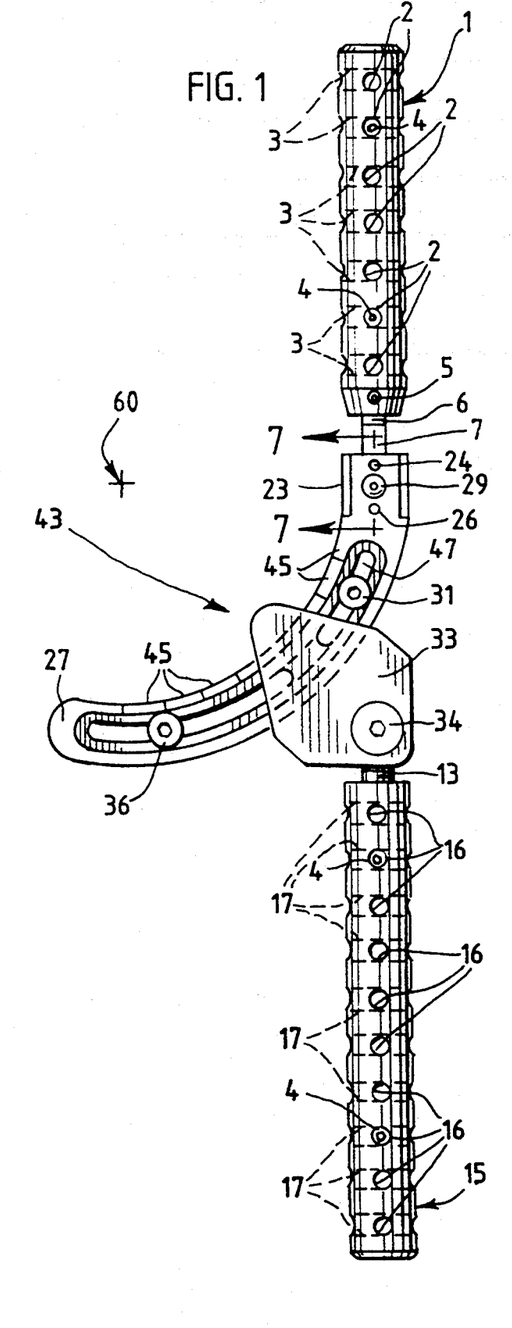
FIG. 1 shows a top view of the present invention in accordance with a preferred embodiment.
Figure 2:
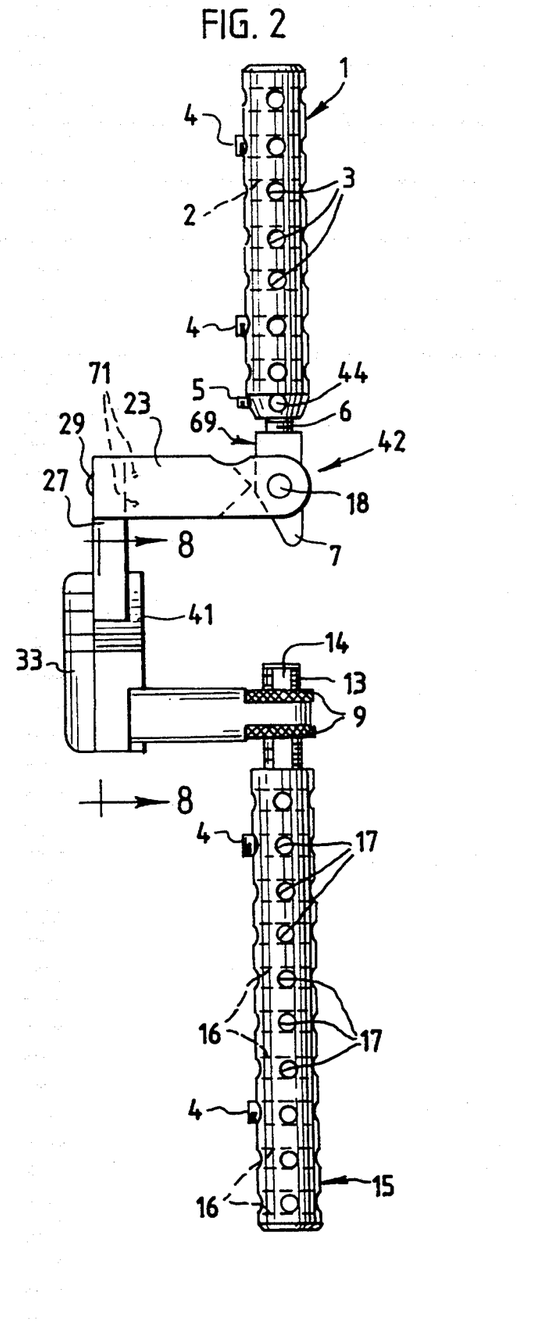
FIG. 2 shows a side view of a dynamic external fixator according to the present invention.
Figure 6:
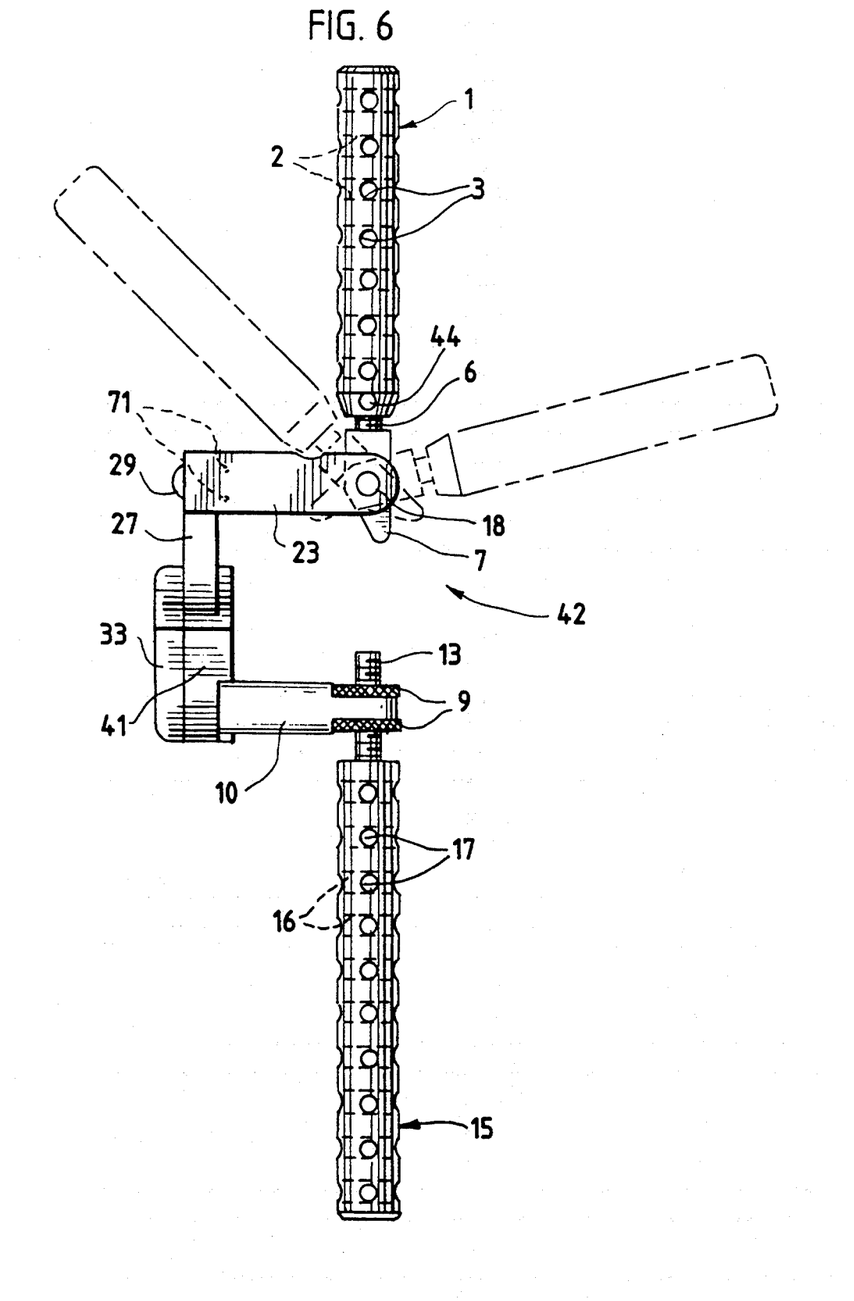
FIG. 6 shows a side view of the dynamic external fixator in flexion and extension.
Figure 7:
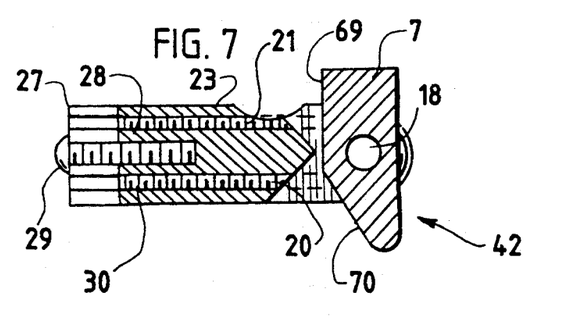
FIG. 7 is a section view taken at 7—7 of FIG. 1 depicting the hinge mechanism between the interconnect piece and distal limb of the external fixator.

The hinge mechanism 42, as illustrated in FIG. 2, is comprised of the proximal end of the distal leg stem 7 of the dynamic external fixator and the lower or palmar end of the distal interconnecting piece 23. As shown, the stem 7 of the distal leg 1 is hingedly secured to the distal interconnecting piece 23 by means of a hinge pin 18 secured at both ends to the interconnecting piece 23. Two setscrews 28, 30 which are disposed within the interconnecting piece 23 provide means for limiting and adjusting the degree of flexion and extension of the distal leg 1 with respect to the interconnecting piece 23. The distal leg stem 7 of the hinge component 18 of the articulating portion preferably include abutment surfaces 69, 70 against which the two setscrews 28, 30 will, respectfully, abut and thereby limit the hinged movement of the distal leg 1 of the dynamic external fixator in flexion 28, 69 and extension 30, 70, as illustrated in FIGS. 6 and 7. Preferably, the setscrews 28, 30 may be adjusted in order to correspondingly adjust the range of flexion and extension. For example, as viewed froIn FIG. 7, if setscrew 30 is "tightened," such that it is disposed in a more palmar position, the maximum degree of flexion will be reduced. The range of movement of the distal leg 1 is shown in FIG. 6.

A preferred method of affixing the dynamic external fixator of the present invention will now be described in conjunction with FIG. 4. The hand and lower arm of the human skeleton consists of the radius 50 and ulna 51, eight carpal bones including the scaphoid 53, lunate 56, triquetrum 57, pisiform (not shown), trapezoid 55, trapezium 54, capitate 59, and hamate 58 bones. The hand consists of the metacarpal bones 61a–e, the proximal phalanges 62a–e, middle phalanges 63b–e, and distal phalanges 64a–e. The distal 1 and proximal 15 legs may be connected to bone fixation pins 52 fixed distally in the patient's metacarpal bone 61b and proximally in the distal shaft of the radius 50 as shown in FIG. 4. In some cases, it may be preferable to affix the distal bone fixation pins 52A into the patient's third metacarpal bone 61c as well as the second metacarpal bone 61b, as shown in FIG. 4. In other cases, however, fixation only in the second metacarpal bone 61b will be sufficient.

When the device of the present invention is affixed to the patient, the movement of the hand distal to the wrist results from the coordination between the normal kinematics of the wrist and the kinematics range of movement defined by the dynamic external fixator when it is attached to the forearm and hand of the patient.

Studies have shown that the center of rotation of the bones of the wrist and hand unit is approximately at the proximal pole of the capirate bone 60. According to an important aspect of the present invention, the external fixator of the present invention is designed with the same center of rotation for its movement. More specifically, the axis 60' of rotation of the track 27 within the track housing 41 (FIG. 5), is aligned with and coaxial to the axis 60 of radial and ulnar deviation of the normal, i.e., without a fracture, human wrist. Likewise, the axis of hinged movement of the distal leg 1 is coplanar with and coaxial to the axis of flexion and extension of the normal human wrist.

In the present invention, therefore, the hinge mechanism 42 of the dynamic external fixator is precisely positioned at the time of affixation to align with the virtual axis of flexion and extension of the wrist, and the center of radius of curvature, or axis 60' of the track-track housing mechanism 43 is positioned to correspond with the axis 60 of radial and ulnar deviation of the wrist. When this is done, the movement of the wrist and fixator are essentially the same, and no abnormal movement of the wrist is allowed.

Figure 10:
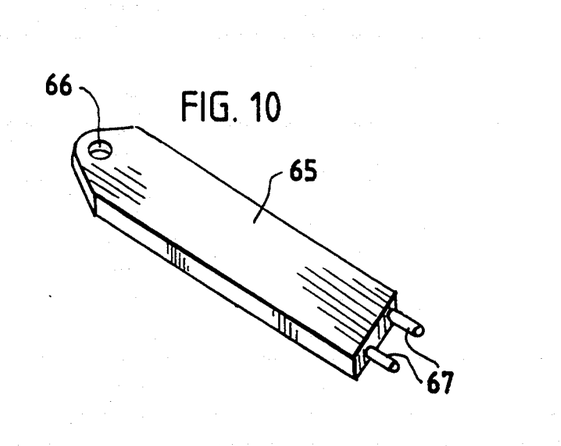
FIG. 10 depicts a targeting guide.

As should now be clear, the external fixator of the present invention should be positioned in a specific relation to the wrist, and this is preferably accomplished by means of an alignment device 65 as shown in FIG. 10. In order to affix the device to the lower arm and hand of the patient, a plurality of elongated bone fixation pins 52 are inserted into the smooth holes 17 of the proximal 15 and the distal legs 1 and securely retained in a particular desired orientation by the setscrews 4 which are screwed into the threaded holes 16 so as to frictionally bear against the elongated bone fixation pins 52. The setscrews 4 may be provided with allen type heads, including a hexagonal recess adapted to receive a tool with a hexagonal periphery, in order to facilitate tightening of the setscrews 4.

The distal leg 1, which includes an arrangement similar to the proximal leg 15, is provided with a plurality of smooth bore holes 3 drilled perpendicularly to threaded bore holes 2 for the purposes of retaining bone fixation pins 52A from the distal leg 1 to the metacarpals 61b,c. After final adjustment, the pins 52A may be secured to the leg 1 by tightening the setscrews 4 against the pins 52A.

According to conventional and well-known techniques, one or more bone fixation pins 52A are inserted into the second metacarpal 61b, as shown in FIG. 4. One end of the pins may be provided with self-tapping continuous threads 68, while the other end may be adapted for secure insertion into a chuck (not shown), in order to facilitate affixation to the bone. Self-tapping thread 68 provides secure gripping power of the bone pin 52A into the second metacarpal 61b. Likewise, the proximal leg 15 is preferably attached by one or more bone fixation pins 52B to the shaft of the radius 50 in a similar manner. The bone pins 52 are then placed into the distal 1 and proximal 15 legs of the dynamic external fixator, respectively, and secured in place by means of setscrews 4 which will securely retain the bone fixation pins 52 to the proximal 15 and distal legs 1 of the fixator.

According to a preferred embodiment, the dynamic external fixator of the present invention is designed to be positioned with the distal 1 and the proximal 15 leg of the device along the radial aspect of the distal forearm and hand as illustrated in FIG. 4. The interconnecting pieces 10, 23 extending from the proximal 15 and distal 1 legs are preferably directed in the dorsal or backward direction, thereby positioning the track-track housing mechanism 43 generally over the back of the hand.

In order to affix bone fixation pins 52 to the bone, a small incision is made through the skin adjacent to the radius 50 or second metacarpal 61b for transcutaneous insertion of the bone fixation pins 52. During affixation, the fracture should be reduced (aligned) under radiographic guidance and held in this position by means of traction in a conventional manner. With the fracture reduced and bone fixation pins 52 inserted into the metacarpal 61b and radius 50, the proximal 15 and distal 1 legs of the dynamic external fixator can be placed in connection with the bone fixation pins 52 and secured in place, as previously described. Again, radiographic guidance is preferably used to assure position and proper distance of the dynamic external fixator such that the axis of radial and ulnar deviation 60 of the hand corresponds to the axis 60' of movement of the track 27 within the track housing 41, as illustrated in FIGS. 4 and 5. This is preferably accomplished with the use of a guide 65, as depicted in FIG. 10, which may be inserted in the inner radius of the interconneting piece 23, as illustrated in FIG. 5. The guide 65 can be inserted by means of pegs 67 which fit into holes 71 in the interconnecting piece 23. The hole 66 in the guide 65 locates the axis 60' of curvature of the curved track 27 and should be placed over the axis 60 of the wrist at the time of application. Thus, after proper affixation the axis of the wrist 60 and the axis 60' of the track 27 will coincide.

Similarly, the axis 60 of flexion and extension of the wrist should be aligned with the axis of flexion and extension of the hinge mechanism 42 of the dynamic external fixator. These positions may be readily verified by radiographic guidance. After affixation of the dynamic external fixator, traction can be removed, and under radiographic guidance the allowable movement of the hand and wrist which does not produce displacement of the fracture fragments can be viewed and determined. The stops 31, 36 of the track 27 should be placed and set to limit the radial and ulnar deviation, as well as the setscrews 28, 30 to limit the range of flexion and extension of the hinged portion 7. Thus, after affixation, movement is limited only to that range which will not result in displacement or malalignment of the fracture itself. As healing progresses, this range of motion may be permitted to be increased so that an increased range of motion will be allowed as the fracture heals and no further displacement of the fracture fragments would result.

What is claimed is:

1. A dynamic external fixation device, adapted to be affixed to a human lower arm and hand, for use in osteosynthesis of a fracture of the distal radius comprising:
   (a) an elongated proximal leg,
   (b) an elongated distal leg,
   (c) proximal affixation means for securely affixing said proximal leg to the distal shaft of the radius
   (d) distal affixation means for securely affixing said distal leg to the metacarpal bone and
   (e) articulating means connected between said proximal leg and said distal leg which defines a first range of movement of fexion and extension having an axis of rotation that approximately passes through the proximal pole of the capitate bone when affixed to the human arm and hand and a second range of movement of radial and ulnar deviation having an axis of rotation spaced from the device and that approximately passes through the proximal pole of the capitate bone when affixed to the human arm and hand.

2. The device as set forth in claim 1 further including means for substantially precluding any movement that deviates from said first range of movement and said second range of movement.

3. The device as set forth in claim 1 further comprising means for limiting said first range of movement to a portion of said first range of movement and means for limiting said second range of movement to a portion of said second range of movement.

4. The device as set forth in claim 1 wherein said articulating means is comprised of:
   an track-track housing mechanism that defines said first range of movement, and
   a hinge mechanism that defines said second range of movement.

5. The device as set forth in claim 4 further comprising an adjustable radial abutment element for limiting the range of radial deviaiton of the wrist, and an adjustable ulnar abutment element for limiting the range of ulnar deviaiton of the wrist.

6. The device as set forth in claim 5 wherein said radial abutment element is adjusted to limit radial deviation to no greater than about 25° and said ulnar abutment element is adjusted to limit ulnar deviation to no greater than about 45°.

7. The device as set forth in claim 4 further comprising an adjustable extension abutment element for limiting the range of extension of the wrist, and an adjustable flexion abutment element for limiting the range of flexion of the wrist.

8. The device as set forth in claim 7 wherein said extension abutment element is adjusted to limit the range of extension to no greater than about 45° and said flexion abutment element is adjusted to limit the range of flexion to no greater than about 45°.

9. The device as set forth in claim 1 wherein said proximal affixation means is comprised of one or more elongated proximal bone fixation pins adapted to be attached at one end to said proximal leg and at the other end to the distal shaft of the radius, and wherein said distal affixation means is comprised of one or more elongated distal bone fixation pins adapted to be attached at one end to said distal leg and at the other end to the second metacarpal bone.

10. The device as set forth in claim 9 further comprising means for rotating said elongated distal leg about its axis in order to attach said distal bone fixation pins at predetermined attached locations on said distal leg.

11. The device as set forth in claim 10 further comprising means for preventing rotation of said distal leg.

12. The device as set forth in claim 1 further comprising means for adjusting the relative distance from said proximal leg to said distal leg.

13. A dynamic external fixation device, adapted to be affixed to the lower arm and hand of a human patient, said device comprising:
- an elongated proximal leg adapted to be securely affixed to the radius of said patient and disposed substantially parallel to the radial aspect of the radius of said patient by a plurality of elongated proximal bone fixation pins,
- an elongated distal leg adapted to be securely affixed to the second metacarpal of said patient by a plurality of elongated distal bone fixation pins,
- a curved track adapted to be dispsoed dorsally of said hand wherein the center of curvature of said track defines a range of radial and ulnar deviation of the wrist with an axis of rotation that approximately passes through the proximal pole of the capitate bone when affixed to the human arm and hand,
- a track housing slidingly engaged upon said curved track wherein said track slides through said track housing about said axis of rotation of said curved track with a predetermined range of rotation defined by said track,
- a proximal interconnect element extending between said proximal leg and said track housing and a distal interconnect element extending between said distal leg and said curved track, said distal interconnect element including hinge means for defining a prdetermined range of hinged movement of said distal leg with respect to said curved track, wherein the range of hinged movement defined by said hinge means has an axis of rotation that approximately passes through the proximal pole of the capitate bone when affixed to the human arm and hand, whereby said proximal and distal interconnect elements transmit the predetermined range of movement defined by said track with respect to said track housing to a corresponding predetermined range of movement of said distal leg with respect to said proximal leg.

14. A dynamic external fixation device as set forth in claim 13 wherein the predetermined range of movement of said track with respect to said track housing substantially precludes movement of the wrist that deviates from movement of flexion and extension having an axis of rotation that approximately passes through the proximal pole of the capitate bone and movement of radial and ulnar deviation having an axis of rotation that approximately passes thorugh the proximal pole of the capitate bone.

15. A dynamic external fixation device as set forth in claim 13 wherein the predetermined range of hinged movement defined by said hinged means substantially precludes movement that deviates movement with an axis that approximately passes through the proximal pole of the capitate bone.

16. A dynamic external fixation device as set forth in claim 12 further comprising means for limiting the predetermined range of rotation defined by said track.

17. A dynamic external fixation device as set forth in claim 13 further comprising means for limiting the predetermined range of hinged movement defined by said hinge means.

18. A dynamic external fixation device as set forth in claim 13 further comprising targeting means for determining the axial position of said curved track with respect to the bone structure of the hand of the patient.

19. A dynamic external fixation device as set forth in claim 13 further comprising targeting means for determining the axial position of said hinge means with respect to the bone structure of the hand of the patient.

20. The dynamic external fixation device as set forth in claim 13 further comprising means for rotating said distal leg about its axis in order to receive and align said distal bone fixation pins toward the metacarpal bone from predetermined attachment locations on said distal leg.

21. The dynamic external fixation device as set forth in claim 20 further comprising means for preventing rotation of said distal leg.

22. The dynamic external fixation device as set forth in claim 13 further comprising means for adjusting the location along said proximal leg at which said proximal interconnect element is connected.

23. A dynamic external fixation device, adapted to be affixed to a human lower arm and hand, for use in osteosynthesis of a fracture of the distal radius comprising:
 (a) an elongated proximal leg,
 (b) an elongated distal leg,
 (c) proximal affixation means for securely affixing said proximal leg to the distal shaft of the radius,
 (d) distal affixation means for securely affixing said distal leg to the metacarpal bone, and
 (e) articulating means, connected between said proximal leg and said distal leg, comprised of a hinge mechanism that defines a first range of movement of flexion and extension having an axis of rotation that approximately passes through the proximal pole of the capitate bone when affixed to the human arm and hand, and a track-track housing mechanism that defines a second range of movement of radial and ulnar deviation having an axis of rotation that approximately passes through the proximal pole of the capitate bone when affixed to the human arm and hand.

24. The device as set forth in claim 23 further comprising an adjustable radial abutment element for limiting the range of radial deviation of the wrist, and an adjustable ulnar abutment element for limiting the range of ulnar deviation of the wrist.

25. The device as set forth in claim 24 wherein said radial abutment element is adjusted to limit radial deviation to no greater than about 25° and said ulnar abutment element is adjusted to limit ulnar deviation to no greater than about 45°.

26. The device as set forth in claim 23 further comprising an adjustable extension abutment element for limiting the range of extension of the wrist, and an adjustable flexion abutment element for limiting the range of flexion of the wrist.

27. The device as set forth in claim 26 wherein said extension abutment element is adjusted to limit the range of extension to no greater than about 45° and said flexion abutment element is adjusted to limit the range of flexion to no greater than about 45°.

28. A dynamic external fixation device, adapted to be affixed to the lower arm and hand of a human patient, said device comprising:

an elongated proximal leg adapted to be securely affixed to the radius of said patient and disposed substantially parallel to the radial aspect of the radius of said patient by a plurality of elongated proximal bone fixation pins, an elongated distal leg adapted to be securely affixed to the second metacarpal of said patient by a plurality of elongated distal bone fixation pins, a curved track adapted to be disposed dorsally of said hand wherein the center of curvature of said track defines a range of radial and ulnar deviation of the wrist with an axis of rotation that approximately passes through the proximal pole of the capitate bone when affixed to the human arm and hand, a track housing slidingly engaged upon said curved track wherein said track slides through said track housing about said axis of said curved track with a predetermined range of rotation defined by said track, a proximal interconnect element extending between said proximal leg and said track housing, and a distal interconnect element extending between said distal leg and said curved track, said distal interconnect element having hinge means for defining a predetermined range of hinged movement of said distal leg with respect to said distal interconnect element, wherein the range of hinged movement defined by said hinge means has an axis of rotation that approximately passes through the proximal pole of the capitate bone when affixed to the human arm and hand, and wherein said hinge means defines a range of flexion and extension, whereby said proximal and distal interconnect elements transmit the predetermined range of movement defined by said track with respect to said track housing to a corresponding predetermined range of movement of said distal leg with respect to said proximal leg.

29. A dynamic external fixation device as set forth in claim 28 wherein the predetermined range of hinged movement defined by said hinged means substantially precludes movement that deviates from movement with an axis that approximately passes through the proximal pole of the capitate bone.

30. A dynamic external fixation device as set forth in claim 28 comprising means for limiting the predetermined range of hinged movement defined by said hinge means.

31. A dynamic external fixation device as set forth in claim 28 further comprising targeting means for determining the axial position of said hinge means with respect to the bone structure of the hand of the patient.

32. A method for attaching to a human lower arm and hand a dynamic external fixation device for use in osteosynthesis of a fracture of the distal radius, said device comprising:
(a) an elongated proximal leg,
(b) an elongated distal leg,
(c) articulating means connected between said proximal leg and said distal leg which defines a first range of movement of radial and ulnar deviation having an axis of rotation spaced from the device, the method comprising:
affixing said elongated proximal leg to the distal shaft of the radius,
affixing said elongated distal leg of the metacarpal bone, and
positioning said articulating means such that the axis of rotation of said articulating means passes approximately through the proximal pole of the capitate bone.

33. The method of claim 32 wherein said articulating means further defines a second range of movement of flexion and extension having an axis of rotation that precisely passes through the proximal pole of the capitate bone when affixed to the human arm and hand.

34. A method for attaching to the human lower arm and hand a dynamic external fixation device, for use in osteosynthesis of a fracture of the distal radius, said device comprising:
(a) an elongated proximal leg,
(b) an elongated distal leg,
(c) articulating means connected between said proximal leg and said distal leg which defines a first range of movement of radial and ulnar deviation having a first axis of rotation spaced from the device, the method comprising:
affixing said elongated proximal leg to the distal shaft of the radius,
affixing said elongated distal leg to the metacarpal bone, and
positioning said articulating means such that the first axis of rotation of said articulating means passes approximately through the proximal pole of the capitate bone and such that the articulating means precludes radial and ulnar deviation about any axis other than said first axis,
movement about said first axis substantially precluding radial and ulnar deviation about any axis other than said first axis.

35. The method of claim 34 wherein said articulating means further defines a second range of movement of flexion and extension having a second axis of rotation that precisely passes through the proximal pole of the capitate bone when affixed to the human arm and hand.

* * * * *